(12) United States Patent
Lin

(10) Patent No.: US 10,888,233 B2
(45) Date of Patent: Jan. 12, 2021

(54) MONOPOLAR PHYSIOLOGICAL SIGNAL DETECTION DEVICE AND ITS OPERATING METHOD

(71) Applicant: FENG CHIA UNIVERSITY, Taichung (TW)

(72) Inventor: Yue-Der Lin, Taichung (TW)

(73) Assignee: FENG CHIA UNIVERSITY, Taichung (TW)

( * ) Notice: Subject to any disclaimer, the term of this patent is extended or adjusted under 35 U.S.C. 154(b) by 136 days.

(21) Appl. No.: 16/237,729

(22) Filed: Jan. 1, 2019

(65) Prior Publication Data
US 2020/0037900 A1 Feb. 6, 2020

(30) Foreign Application Priority Data
Aug. 2, 2018 (TW) .............................. 107126971 A

(51) Int. Cl.
*A61B 5/0428* (2006.01)
*A61B 5/024* (2006.01)
*A61B 5/0408* (2006.01)

(52) U.S. Cl.
CPC ...... *A61B 5/02405* (2013.01); *A61B 5/02438* (2013.01); *A61B 5/0408* (2013.01); *A61B 5/0428* (2013.01); *A61B 2562/14* (2013.01)

(58) Field of Classification Search
CPC ............ A61B 2562/14; A61B 5/02108; A61B 5/02405; A61B 5/02416; A61B 5/02438; A61B 5/0245; A61B 5/0408; A61B 5/0428
See application file for complete search history.

(56) References Cited

U.S. PATENT DOCUMENTS

| 4,181,134 A * | 1/1980 | Mason ............... A61B 5/02438 600/502 |
| 2015/0200637 A1* | 7/2015 | Ko ........................ H03F 1/0277 330/9 |

FOREIGN PATENT DOCUMENTS

| CN | 100423688 C | 10/2008 |
| CN | 103654766 A | 3/2014 |
| CN | 104274906 A | 1/2015 |
| CN | 106354386 A | 1/2017 |
| CN | 107822626 A | 3/2018 |

\* cited by examiner

*Primary Examiner* — George Manuel
(74) *Attorney, Agent, or Firm* — Cheng-Ju Chiang

(57) ABSTRACT

A monopolar physiological signal detection device and a method of operating the monopolar physiological signal detection device are provided. With a differential amplifier, a delay circuit, a driven-body circuit, and a band-pass filter, the monopolar physiological signal detection device can reduce the common-mode interference induced by supply mains. Moreover, the monopolar physiological signal detection device employs a single electrode to generate electric potentials with different time factors from the same skin surface. Accordingly, consecutive heartbeat related information of a user can be collected even when the user is under natural and comfortable postures.

11 Claims, 2 Drawing Sheets

MONOPOLAR PHYSIOLOGICAL SIGNAL DETECTION DEVICE AND ITS OPERATING METHOD

CROSS-REFERENCE TO RELATED APPLICATION AND CLAIM OF PRIORITY

This application claims the benefit of Taiwanese Patent Application No. 107126971, filed on Aug. 2, 2018, in the Taiwan Intellectual Property Office, the disclosure of which is incorporated herein in its entirety by reference.

1. TECHNICAL FIELD

At least one embodiment of the present invention provides a monopolar physiological signal detection device and a method of operating the monopolar physiological signal detection device. More particularly, it is related to a monopolar physiological signal detection device which deploys an electrode attached on any limb to read and monitor the heartbeat-related information such as heart rate of a user, and the method of operating such monopolar physiological signal detection device.

2. DESCRIPTION OF THE RELATED ART

Heart rate can be used to detect cardiovascular or non-cardiovascular diseases, such as myocardial infarction, heart arrhythmia, cardiac arrest, and psychological status. However, such attempts require long-term monitoring to meet this intended use under real-world clinical settings.

The current approaches to monitor heart rate are widely relying on optical pulse sensor module installed in wearable devices. However, the performance of optical pulse sensor module is easily affected by ambient light, postures, skin colors, wrist sizes, and even breath. With the weak signals generated by such devices, measuring heart rate is extremely difficult in some populations.

In order to obtain precise and reliable information, users are asked to maintain still during the measurement if they are using wearable devices based on the optical pulse sensor module. Such requirement limits the applications of optical pulse sensor module in a real-world context. There are some other pulse monitors that are independent of the optical mechanism, but they require the user to touch, with a finger of the free hand, a second contact site on the wearable devices to obtain accurate data.

As both hands are required during the monitoring, it is exceptionally unrealistic to use these devices because they need the users to stay in the same posture as long as they want to monitor their heart rate. The unnatural postures also make variability analysis on heart rate impossible because such posture would interfere with the normal neuron activities.

Since the supply mains usually is an alternative current at 50 Hz or 60 Hz, the electromagnetic waves and electrical fields generated by the supply mains can easily interfere with the potential signals of heartbeat or heart rate detected by the above devices. Furthermore, the interference from the alternative current, either at 50 Hz or 60 Hz, is a common-mode interference, which is deemed to have the same impact on each part of the body due to its long wavelength.

SUMMARY

At least one embodiment of the present invention is provided to resolve the challenges confronted by the prior arts. In the embodiment, a monopolar physiological signal detection device comprising a detection area, a differential amplifier, a delay circuit, a driven-body circuit, a band-pass filter, and an output is disclosed.

The detection area is configured to be in contact with a detectable site. As for the differential amplifier, it is connected with the detection area through a first wire and a second wire separately, in which the delay circuit is configured on the first wire. The driven-body circuit is also connected with the detection area. However, the driven-body circuit is connected with the differential amplifier through a plurality of resistors at the same time. On the other hand, the band-pass filter is connected with the differential amplifier while the output is in connection with the band-pass filter.

At least one embodiment of the present invention provides a method of operating such monopolar physiological signal detection device. In the first step, a monopolar physiological signal detection device in the previous embodiment is provided. A detection area on the monopolar physiological signal detection device subsequently obtains an electrical heartbeat signal and a common-mode interference signal from a detectable site.

Then, the electrical heartbeat signal and the common-mode interference signal are transmitted to the delay circuit through the first wire and to the positive input terminal of the differential amplifier through the second wire respectively. In the next step, a time delay is generated by the delay circuit and introduced the time delay into the electrical heartbeat signal to form a delayed electrical heartbeat signal. The delayed electrical heartbeat signal is subsequently transmitted to the negative input terminal of the differential amplifier.

The driven-body circuit, on the other hand, generates a suppressed common-mode interference signal and transmits the suppressed common-mode interference signal to the differential amplifier through several resistors. The differential amplifier accordingly amplifies the electrical heartbeat signal, the delayed electrical heartbeat signal, the common-mode interference signal, and the suppressed common-mode interference signal and then transmits them to the band-pass filter to obtain a resulted heartbeat signal. In the final step, the resulted heartbeat signal is transmitted to the output.

There are many inventions described and illustrated herein. The present inventions are neither limited to any single aspect nor embodiment thereof, nor to any combinations and/or permutations of such aspects and/or embodiments. Moreover, each of the aspects of the present inventions, and/or embodiments thereof, may be employed alone or in combination with one or more of the other aspects of the present inventions and/or embodiments thereof. For the sake of brevity, many of those permutations and combinations will not be discussed separately herein.

DESCRIPTION OF THE PREFERRED EMBODIMENTS

The drawings disclose some preferred embodiments of the present invention, which are intended to be used with the descriptions herein to enable one skilled in the art to understand the claimed features, as well as to make and use the claimed invention.

Figure 1:
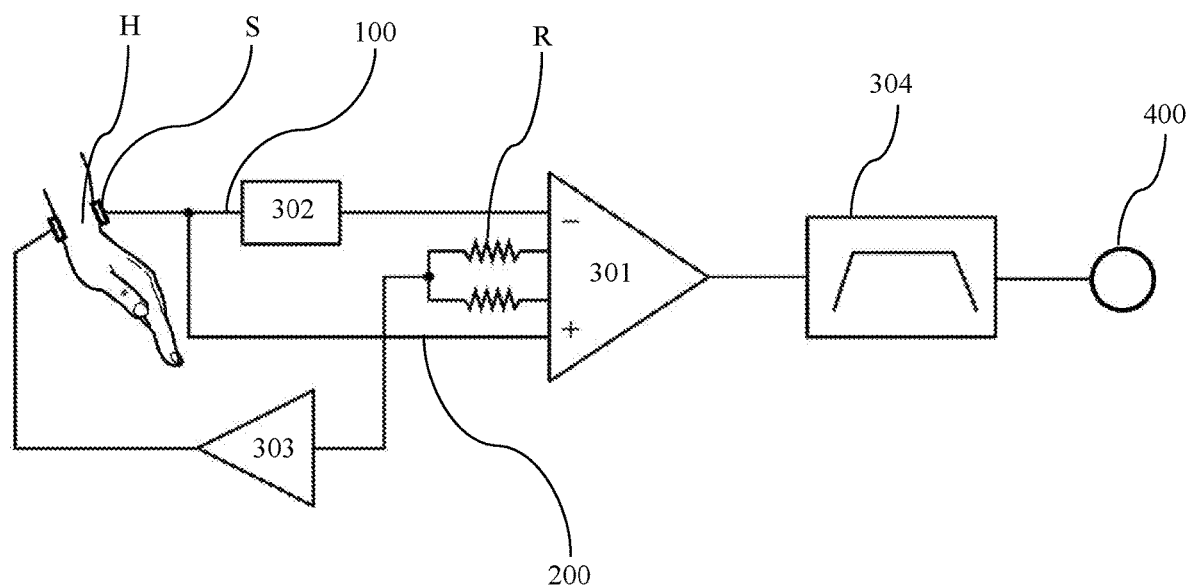
FIG. 1 is a schematic diagram illustrating an integrated circuit, in accordance with some embodiments of the present invention.

FIG. 1 is a schematic diagram illustrating an integrated circuit, in accordance with some embodiments of the present invention. In FIG. 1, a monopolar physiological signal detection device 10 is disclosed. The monopolar physiological signal detection device 10 comprises a detection area S, a differential amplifier 301, a delay circuit 302, a driven-body circuit 303, a band-pass filter 304, and an output 400.

The detection area S in FIG. 1 could be a single electrode, such as a metallic electrode or a carbon electrode. The detection area S is configured to be in contact with a detectable site H, which is the wrist of a person in FIG. 1. As the embodiment may be comprised in the band or a strap of a wearable device and a wearable device usually only contains a positive voltage source, the embodiment is based on a similar design with only a positive voltage source and operating on a direct current at 2.5 V or above. However, the present invention is not limited by this embodiment. Similarly, the detectable site H is not limited by this embodiment and may be any part of a human body like arms or ankles.

In the present embodiment of FIG. 1, the differential amplifier 301 is preferred to be a high-CMRR/high-input-impedance differential amplifier.

The differential amplifier 301 is connected with the detection area S through a first wire 100 and a second wire 200 separately. More particularly, the first wire 100 is connected to a first input (i.e., the negative input terminal of the differential amplifier 301 in FIG. 1) of the differential amplifier 301 and the second wire 200 is connected with a second input (i.e., the positive input terminal of the differential amplifier 301 in FIG. 1) of the differential amplifier 301.

Note that in FIG. 1, the delay circuit 302 is configured on the first wire 100. The driven-body circuit 303 is directly connected to the detection area S but connected to the differential amplifier 301 through a plurality of resistors R. Here in FIG. 1, the driven-body circuit 303 is a body potential driver circuit.

In the embodiment, the body potential driver circuit is a biosignal amplifier which can be configured on any part of the human body (e.g., the detectable site S in the embodiment, which is configured on the opposite sites of the wrist). As the supply mains, an alternating current (AC) at 50 or 60 Hz, produces common-mode interference around the environment of a subject, the biosignal amplifier is employed to mitigate such interference. The driven-body circuit 303 here is used to provide a reference potential to suppress the common-mode interference induced by the supply mains.

The band-pass filter 304 is connected with the differential amplifier 301 while the output 400 is connected with the band-pass filter 400. As shown in FIG. 1, the embodiment also comprises a display connected with the output 400, in which the display is configured to display information pertaining to the heartbeat related information. The embodiment provides a hint that the monopolar physiological signal detection device 10 could be, but not limited to, a tablet, a laptop, a wearable device, or a smartphone.

In some alternative embodiments, the output 400 is further combined to a signal integration module with an optical pulse sensor module. In these embodiments, the signal integration module could be a digital/analog signal processor. The signal integration module is configured to process the profile of the heartbeat signal generated by the monopolar physiological signal detection device 10 and the profile of the optical pulse signal generated by the optical pulse sensor module. The combination of such two profiles provides a more precise heart rate monitoring. By comparing the peaks of the two profiles over time, the observed difference in time can also be used to estimate blood pressures. However, the present inventions should not be limited to the above applications.

Figure 2:
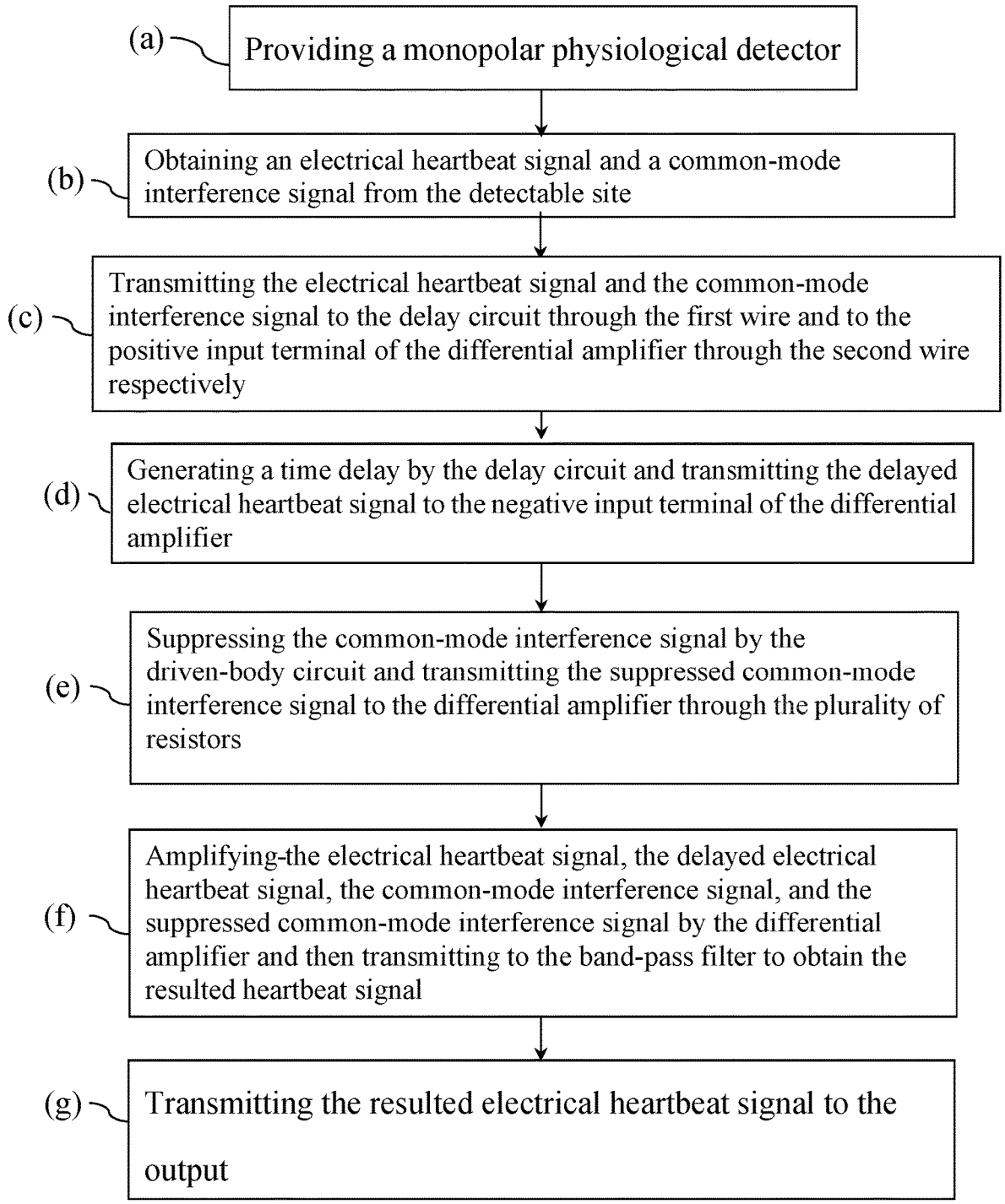
FIG. 2 is a flow chart illustrating a method, in accordance with one embodiment of the present invention.

The monopolar physiological signal detection device 10 in FIG. 1 can be operated by the method shown in FIG. 2. FIG. 2 is a flow chart illustrating a method, in accordance with one embodiment of the present invention. As in FIG. 2, the method of operating a monopolar physiological signal detection device 10 comprises, from step (a) to step (g), seven steps.

Step (a) is providing the monopolar physiological signal detection device disclosed in the previous embodiments. Then, in step (b), an electrical heartbeat signal and a common-mode interference signal are obtained from a detectable site H by a detection area S.

In such embodiments, $V_b(t)$ and $V_{cm}$ denote the electrical heartbeat signal and the common-mode interference signal respectively. In some preferred embodiments, $V_b(t)$, the electrical heartbeat signal, is at around 1 Hz and $V_{cm}$, the common-mode interference signal, is at 50 Hz or 60 Hz.

Step(c) is to transmit the electrical pulse signal and the common-mode interference signal to a delay circuit 302 through a first wire 100. In the same step, the electrical heartbeat signal and the common-mode interference signal are also transmitted to the positive input terminal of a differential amplifier 301 through a second wire 200. Following step(c), a delay circuit 302 first generates a time delay and converts the electrical heartbeat signal into a delayed electrical heartbeat signal according to the time delay in step (d). And in the second part of step (d), the delay circuit 302 delivers the delayed electrical heartbeat signal to the negative input terminal of the differential amplifier 301.

In step (d), the delay time generated by the delay circuit 302 is denoted as τ. That is, by step (c) and step (d), the first potential $(V_b(t)+V_{cm})$, from the electrical heartbeat signal $V_b(t)$ and the common-mode interference signal $V_{cm}$ obtained by the detected area S, are transformed into a second potential $(V_b(t-\tau)+V_{cm})$, from the delayed electrical heartbeat signal $V_b(t-\tau)$ and the common-mode interference signal $V_{cm}$, after passing through the delay circuit 302. The differential amplifier 301, a high-CMRR/high-input-impedance differential amplifier, is then used to amplify the potential difference between the first potential $(V_b(t)+V_{cm})$ and the second potential $(V_b(t-\tau)+V_{cm})$.

However, the frequency of the second potential $(V_b(t-\tau)+V_{cm})$ remains at 50 Hz or 60 Hz after such amplification. Accordingly, a suppressed common-mode interference signal is generated and suppressed from the detection area S by a driven-body circuit 303, and transmitted to the differential amplifier 301 through a plurality of resistors 301 in step (e).

Provided that the driven-body circuit 303 is a body potential driver circuit in the embodiments, the driven-body circuit 303 connected with the detection area S can be used to provide a reference potential to suppress the common-mode interference $V_{cm}$ induced by the supply mains, which is an alternating current at 50 or 60 Hz.

To further suppress the noises, the differential amplifier 301 transmits the electrical pulse signal $V_b(t)$, the delayed electrical heartbeat signal $V_b(t-\tau)$, the common-mode interference signal $V_{cm}$, and the suppressed common-mode interference signal to a band-pass filter 400 to obtain a resulted heartbeat signal in step(f). The resulted heartbeat signal is then delivered to an output in step (g).

There are many inventions described and illustrated above. The present inventions are neither limited to any single aspect nor embodiment thereof, nor to any combinations and/or permutations of such aspects and/or embodiments. For the sake of brevity, many of those permutations and combinations will not be discussed separately herein.

What is claimed is:

1. A monopolar physiological signal detection device, comprising:
   a detection area, configured to be in contact with a detectable site;
   a differential amplifier, connected with the detection area through a first wire and a second wire separately;
   a delay circuit, connected with the first wire;
   a driven-body circuit, connected with the detection area, wherein the driven-body circuit is connected with the differential amplifier through a plurality of resistors;
   a band-pass filter, connected with the differential amplifier;
   an output, connected with the band-pass filter;
   a signal integration module, connected with the output; and
   wherein the signal integration module is connected with an optical pulse sensor module.

2. The monopolar physiological signal detection device as claimed in claim 1, wherein the first wire is connected with a first input on the differential amplifier and the second wire is connected with a second input of the differential amplifier.

3. The monopolar physiological signal detection device as claimed in claim 2, wherein the first input is a negative input terminal of the differential amplifier, and wherein the second input is a positive input terminal of the differential amplifier.

4. The monopolar physiological signal detection device as claimed in claim 1, wherein the differential amplifier is high-CMRR/high-input-impedance differential amplifier.

5. The monopolar physiological signal detection device as claimed in claim 1, wherein the driven-body circuit is a body potential driver circuit.

6. The monopolar physiological signal detection device as claimed in claim 1, wherein the monopolar physiological signal detection device is a tablet, a laptop, a wearable device, or a smartphone.

7. The monopolar physiological signal detection device as claimed in claim 1, wherein the output is connected with a display.

8. A method of operating a monopolar physiological signal detection device, comprising:
   providing the monopolar physiological signal detection device as claimed in claim 1;
   obtaining, by the detection area, an electrical heartbeat signal and a common-mode interference signal from the detectable site;
   transmitting the electrical heartbeat signal and the common-mode interference signal to the delay circuit through the first wire and to the positive input of the differential amplifier through the second wire respectively;
   generating, by the delay circuit, a time delay, and converting the electrical heartbeat signal delivered to the delay circuit to a delayed electrical heartbeat signal and transmitting the delayed electrical heartbeat signal to the negative input terminal of the differential amplifier;
   suppressing, by the driven-body circuit, a suppressed common-mode interference signal and transmitting the suppressed common-mode interference signal to the differential amplifier through the plurality of resistors;
   amplifying, by the differential amplifier, the electrical heartbeat signal, the delayed electrical heartbeat signal, the common-mode interference signal, and the suppressed common-mode interference signal and then transmitting to the band-pass filter to obtain a resulted heartbeat signal; and
   transmitting the resulted heartbeat signal to the output.

9. The method of operating a monopolar physiological signal detection device as claimed in claim 8, wherein the first wire is connected with the negative input terminal of the differential amplifier and the second wire is connected with the positive input terminal of the differential amplifier.

10. The method of operating a monopolar physiological signal detection device as claimed in claim 8, wherein the differential amplifier is high-CMRR/high-input-impedance differential amplifier.

11. The method of operating a monopolar physiological signal detection device as claimed in claim 10, wherein the driven-body circuit is a body potential driver circuit.

* * * * *